United States Patent
Donovan

(10) Patent No.: US 6,464,188 B1
(45) Date of Patent: Oct. 15, 2002

(54) NUTRIENT FEEDING SUPPORT APPPARATUS

(76) Inventor: James L. Donovan, 115 B N. Palm Dr., Satellite Beach, FL (US) 32937

( * ) Notice: Subject to any disclaimer, the term of this patent is extended or adjusted under 35 U.S.C. 154(b) by 14 days.

(21) Appl. No.: 09/684,481

(22) Filed: Oct. 6, 2000

(51) Int. Cl.[7] ................................................. A47G 1/10
(52) U.S. Cl. ............................... 248/316.1; 248/311.3; 248/314; 248/125.1; 248/315
(58) Field of Search ............................ 248/311.3, 314, 248/315, 125.1, 125, 316.1, 911, 229.16, 229.29, 219.4; 5/503.1, 508.1

(56) References Cited

U.S. PATENT DOCUMENTS

| | | | |
|---|---|---|---|
| 2,696,963 A | * 12/1954 | Shepard | ....................... 248/229 |
| 4,030,690 A | 6/1977 | Hanauer et al. | |
| 4,338,935 A | 7/1982 | Wilson | |
| 4,489,454 A | * 12/1984 | Thompson | ....................... 5/503 |
| 4,511,157 A | * 4/1985 | Wilt, Jr. | ....................... 280/289 |
| 4,511,158 A | * 4/1985 | Varga et al. | ................. 280/292 |
| D295,315 S | 4/1988 | Nelson | |
| 5,219,428 A | 6/1993 | Stern | |
| 5,358,205 A | 10/1994 | Starkey et al. | |
| 5,685,843 A | 11/1997 | Benhorning | |
| 5,829,723 A | 11/1998 | Brunner et al. | |
| 6,155,760 A | * 12/2000 | Cannelli, Jr. | ................. 409/276 |
| 6,179,260 B1 | * 1/2001 | Ohanian | ................. 248/229.16 |

* cited by examiner

Primary Examiner—Kimberly T. Wood

(57) ABSTRACT

A nutrient feeding support apparatus for providing an effective and efficient manner of securing a feeding syringe or tube. The nutrient feeding support apparatus includes a bracket assembly including a first bracket and a second bracket which is removably mounted to the first bracket and which is adapted to be removably mounted to a bed; and also includes a support assembly including an elongate member upon which the first bracket is adjustably and securely mounted, and also including a feeding device support member being securely attached to a top end of the elongate member, and further including a support adapter being removably mounted to the feeding device support member for supporting a feeding device.

4 Claims, 3 Drawing Sheets

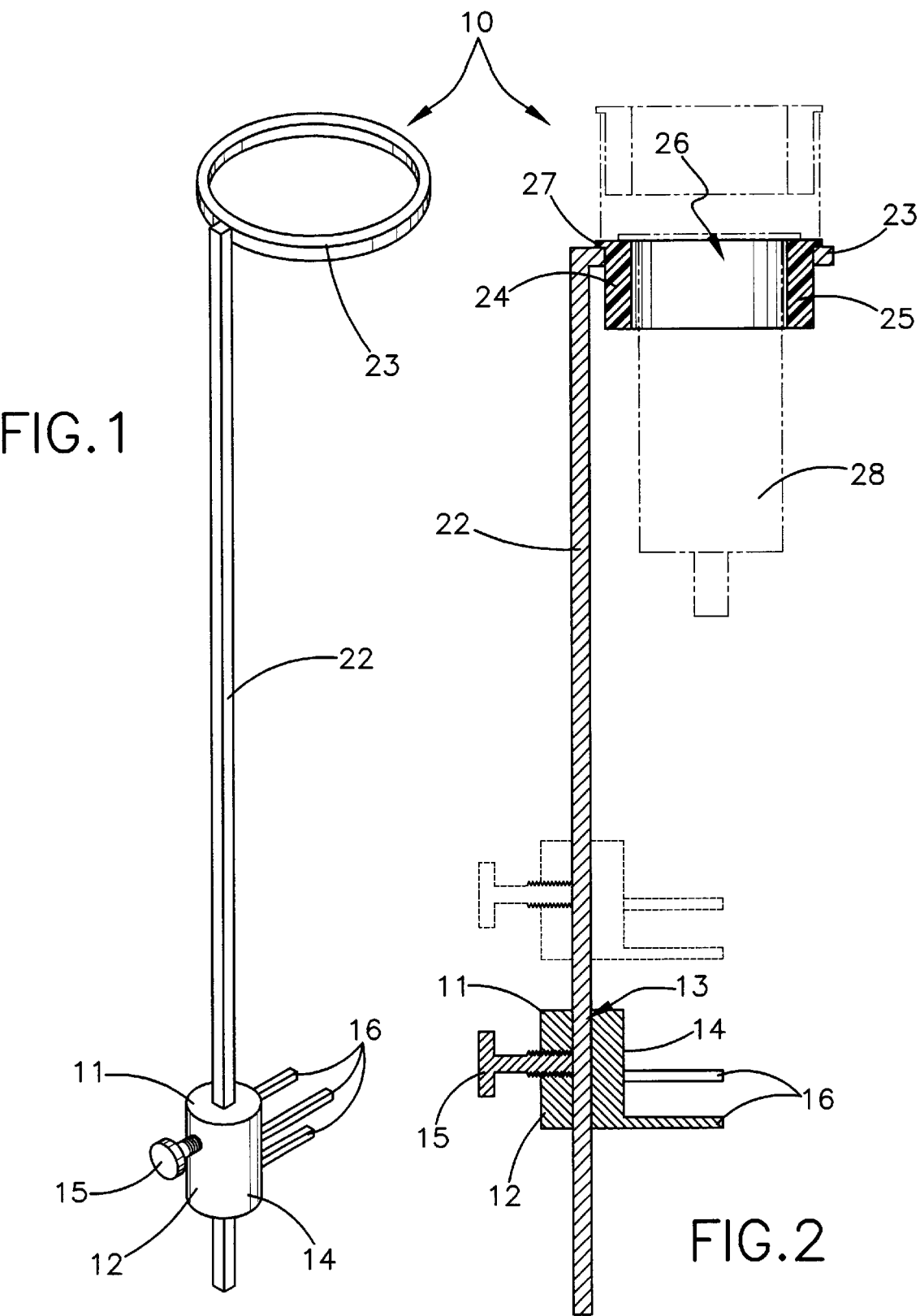

NUTRIENT FEEDING SUPPORT APPPARATUS

BACKGROUND OF THE INVENTION

1. Field of the Invention

The present invention relates to an infant feeding support and more particularly pertains to a new nutrient feeding support apparatus for providing an effective and efficient manner of securing a feeding syringe or tube.

2. Description of the Prior Art

The use of an infant feeding support is known in the prior art. More specifically, an infant feeding support heretofore devised and utilized are known to consist basically of familiar, expected and obvious structural configurations, notwithstanding the myriad of designs encompassed by the crowded prior art which have been developed for the fulfillment of countless objectives and requirements.

Known prior art includes U.S. Pat. Nos. 4,338,935; 5,358,205; 4,030,690; 5,829,723; 5,219,428; U.S. Pat. No. Des. 295,315; and U.S. Patent No. 5,685,843.

While these devices fulfill their respective, particular objectives and requirements, the aforementioned patents do not disclose a new nutrient feeding support apparatus. The inventive device includes a bracket assembly including a first bracket and a second bracket which is removably mounted to the first bracket and which is adapted to be removably mounted to a bed; and also includes a support assembly including an elongate member upon which the first bracket is adjustably and securely mounted, and also including a feeding device support member being securely attached to a top end of the elongate member, and further including a support adapter being removably mounted to the feeding device support member for supporting a feeding device.

In these respects, the nutrient feeding support apparatus according to the present invention substantially departs from the conventional concepts and designs of the prior art, and in so doing provides an apparatus primarily developed for the purpose of providing an effective and efficient manner of securing a feeding syringe or tube.

SUMMARY OF THE INVENTION

In view of the foregoing disadvantages inherent in the known types of infant feeding support now present in the prior art, the present invention provides a new nutrient feeding support apparatus construction wherein the same can be utilized for providing an effective and efficient manner of securing a feeding syringe or tube.

The general purpose of the present invention, which will be described subsequently in greater detail, is to provide a new nutrient feeding support apparatus which has many of the advantages of the infant feeding support mentioned heretofore and many novel features that result in a new nutrient feeding support apparatus which is not anticipated, rendered obvious, suggested, or even implied by any of the prior art infant feeding support, either alone or in any combination thereof.

To attain this, the present invention generally comprises a bracket assembly including a first bracket and a second bracket which is removably mounted to the first bracket and which is adapted to be removably mounted to a bed; and also includes a support assembly including an elongate member upon which the first bracket is adjustably and securely mounted, and also including a feeding device support member being securely attached to a top end of the elongate member, and further including a support adapter being removably mounted to the feeding device support member for supporting a feeding device.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new nutrient feeding support apparatus which has many of the advantages of the infant feeding support mentioned heretofore and many novel features that result in a new nutrient feeding support apparatus which is not anticipated, rendered obvious, suggested, or even implied by any of the prior art infant feeding support, either alone or in any combination thereof.

It is another object of the present invention to provide a new nutrient feeding support apparatus which may be easily and efficiently manufactured and marketed.

It is a further object of the present invention to provide a new nutrient feeding support apparatus which is of a durable and reliable construction.

An even further object of the present invention is to provide a new nutrient feeding support apparatus which is susceptible of a low cost of manufacture with regard to both materials and labor, and which accordingly is then susceptible of low prices of sale to the consuming public, thereby making such nutrient feeding support apparatus economically available to the buying public.

Still yet another object of the present invention is to provide a new nutrient feeding support apparatus which provides in the apparatuses and methods of the prior art some of the advantages thereof, while simultaneously overcoming some of the disadvantages normally associated therewith.

Still another object of the present invention is to provide a new nutrient feeding support apparatus for providing an effective and efficient manner of securing a feeding syringe or tube.

Yet another object of the present invention is to provide a new nutrient feeding support apparatus which includes a bracket assembly including a first bracket and a second bracket which is removably mounted to the first bracket and which is adapted to be removably mounted to a bed; and also includes a support assembly including an elongate member upon which the first bracket is adjustably and securely mounted, and also including a feeding device support member being securely attached to a top end of the elongate member, and further including a support adapter being removably mounted to the feeding device support member for supporting a feeding device.

Still yet another object of the present invention is to provide a new nutrient feeding support apparatus that is easy and convenient to secure to an infant isolette.

Even still another object of the present invention is to provide a new nutrient feeding support apparatus that is adapted to secure to either the top or side of the infant isolette to ensure continual flow of nutrients through the feeding device and feeding tubes to the child.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is a perspective view of a new nutrient feeding support apparatus according to the present invention.

FIG. 2 is a cross-sectional view of the present invention.

DESCRIPTION OF THE PREFERRED EMBODIMENT

Figure 3:
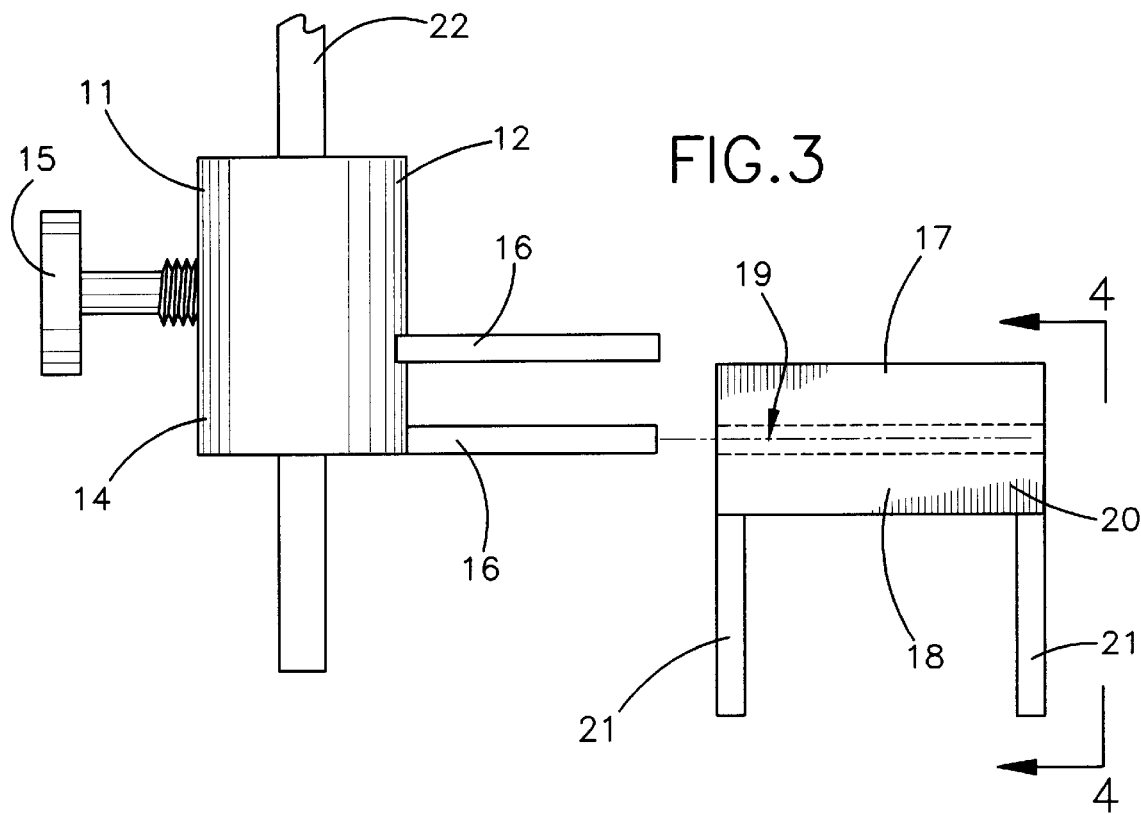
FIG. 3 is a detailed side elevational view of the bracket assembly of the present invention.
Figure 4:
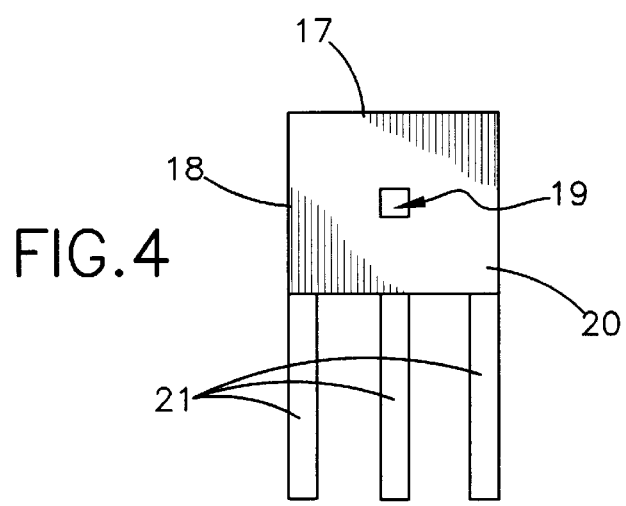
FIG. 4 is an end elevational view of the second bracket of the present invention.
Figure 5:
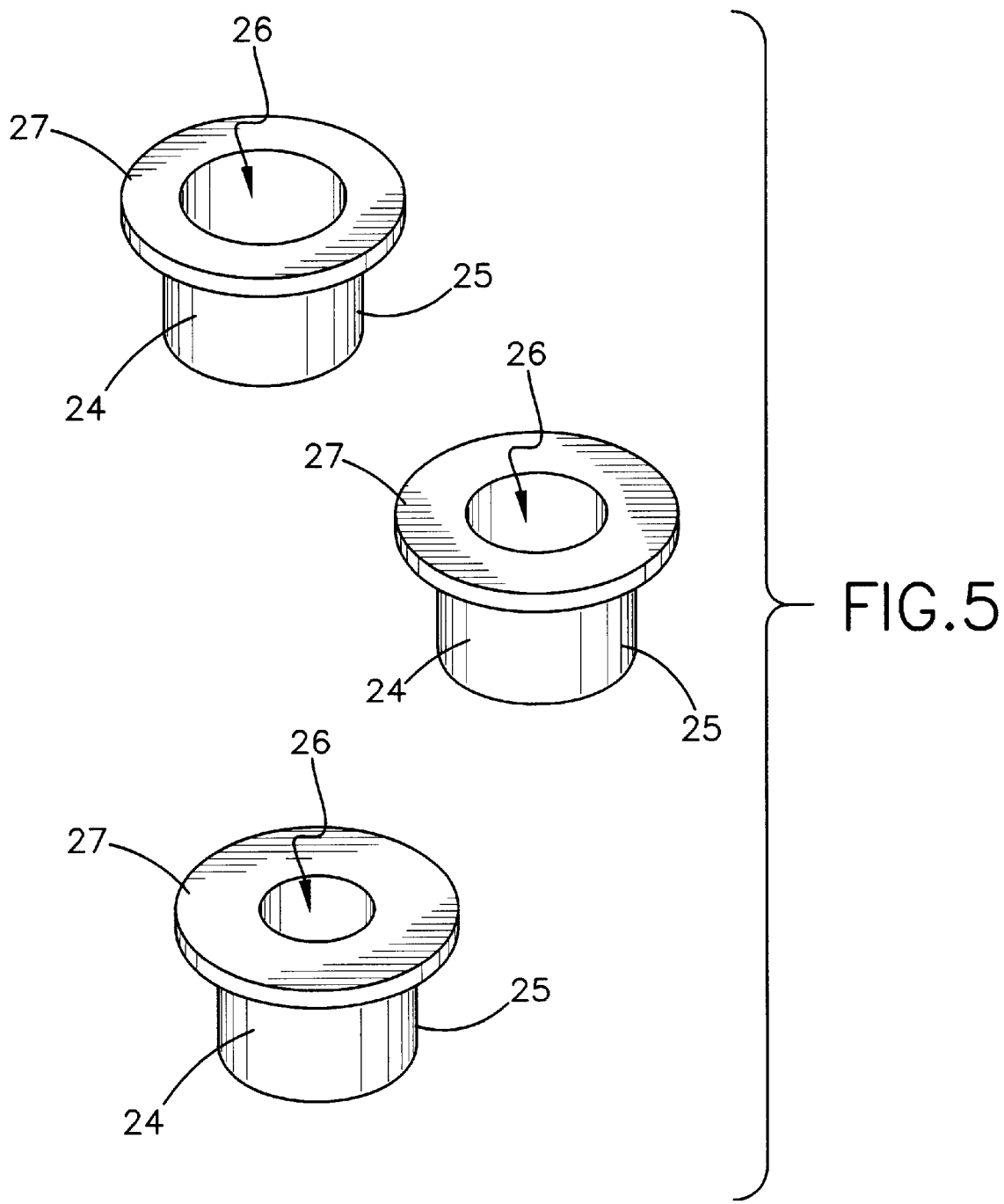
FIG. 5 is a perspective view of the feeding device support members of the present invention.

With reference now to the drawings, and in particular to FIGS. 1 through 5 thereof, a new nutrient feeding support apparatus embodying the principles and concepts of the present invention and generally designated by the reference numeral 10 will be described.

As best illustrated in FIGS. 1 through 5, the nutrient feeding support apparatus 10 generally comprises a bracket assembly including a first bracket 11 and a second bracket 17 which is removably mounted to the first bracket 11 and which is adapted to be removably mounted to a bed. The first bracket 11 includes a cylindrical member 12 having a bore 13 extending therethrough and also having a plurality of prongs 16 being spaced apart and extending outwardly in a generally same direction as one another from a side wall 14 of the cylindrical member 12, and further having a threaded member 15 being threaded through the side wall 14 of the cylindrical member 12 and into the bore 13. The second bracket 17 includes a main member 18 having a bore 19 extending therethrough, and also includes a plurality of prongs 21 being spaced apart and extending outwardly in a generally same direction as to one another from a side wall 20 of the main member 18. The bore 19 of the main member 18 is adapted to receive one of the prongs 16 of the first bracket 11 with the other of the prongs 16 of the first bracket 11 being removably extended about the main member 18. The prongs 21 of the second bracket 17 are adapted to mount into holes of a bed. The bore 19 of the second bracket 17 has a generally square cross-section.

A support assembly includes an elongate member 22 upon which the first bracket 11 is adjustably and securely mounted, and also includes a feeding device support member 23 being securely and conventionally attached and welded to a top end of the elongate member 22, and further includes a support adapter 24 being removably mounted to the feeding device support member 23 for supporting a feeding device 28 such as syringe. The elongate support member 22 is removably and adjustably disposed in the bore 13 of the first bracket 11 and is securely fastened and engaged in the bore 13 of the first bracket 11 with the threaded member 15. The feeding device support member 23 is generally a ring being disposed in a plane which is generally perpendicular to the elongate member 22. The support adapter 24 includes a cylinder 25 having a bore 26 extending therethrough and also has an annular flange 27 being securely and conventionally attached about a rim at a top end of the cylinder 25 and being adapted to rest upon the ring 23 with the bore 26 of the cylinder 24 being adapted to receive and support the feeding device 28. The elongate member 22 has a generally square cross-section.

In use, the second bracket 17 is mounted to a frame of a bed and with the first bracket 11 being mounted to the second bracket 17 and the elongate member 22 being adjustably and securely disposed in the bore 13 of the first bracket 11. If needed, a support adapter 24 is rested upon the ring 23 and the feeding device 28 is supported upon either the ring 23 or the support adapter 24 with a tube being extended to the infant for feeding purposes.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:
1. A nutrient feeding support apparatus comprising:
   a bracket assembly including a first bracket and a second bracket which is removably mounted to said first bracket and which is adapted to be removably mounted to a bed; and a support assembly including an elongate member upon which said first bracket is adjustably and securely mounted, and also including a feeding device support member being securely attached to a top end of said elongate member, and further including a support adapter being removably mounted to said feeding device support member for supporting a feeding device;

wherein said first bracket includes a cylindrical member having a bore extending therethrough, and also having a plurality of prongs being spaced apart and extending outwardly in a generally same direction as one another from a side wall of said cylindrical member, and further having a threaded member being threaded through said side wall of said cylindrical member and into said bore;

wherein said second bracket includes a main member having a bore extending therethrough, and also includes a plurality of prongs being spaced apart and extending outwardly in a generally same direction as to one another from a side wall of said main member, said bore of said main member being adapted to receive one of said prongs of said first bracket with the other of said prongs of said first bracket being extended about said main member, said prongs of said second bracket being adapted to mount into holes of a bed;

wherein said elongate member is removably and adjustably disposed in said bore of said first bracket and is securely fastened and engaged in said bore of said first bracket with said threaded member;

wherein said feeding device support member is generally a ring being disposed in a plane which is generally perpendicular to said elongate member;

wherein said support adapter includes a cylinder having a bore extending therethrough and also having an annular flange being attached about a rim at a top end of said cylinder and being adapted to rest upon said ring with said bore of said cylinder being adapted to receive and support a feeding device.

2. A nutrient feeding support apparatus as described in claim 1, wherein said bore of said second bracket has a generally square cross-section.

3. A nutrient feeding support apparatus as described in claim 1 wherein said elongate member has a generally square cross-section.

4. A nutrient feeding support apparatus comprising:

a bracket assembly including a first bracket and a second bracket which is removably mounted to said first bracket and which is adapted to be removably mounted to a bed, said first bracket including a cylindrical member having a bore extending therethrough, and also having a plurality of prongs being spaced apart and extending outwardly in a generally same direction as one another from a side wall of said cylindrical member, and further having a threaded member being threaded through said side wall of said cylindrical member and into said bore, said second bracket including a main member having a bore extending therethrough, and also including a plurality of prongs being spaced apart and extending outwardly in a generally same direction as to one another from a side wall of said main member, said bore of said main member being adapted to receive one of said prongs of said first bracket with the other of said prongs of said first bracket being extended about said main member, said prongs of said second bracket being adapted to mount into holes of a bed, said bore of said second bracket having a generally square cross-section; and support assembly including an elongate member upon which said first bracket is adjustably and securely mounted, and also including a feeding device support member being securely attached to a top end of said elongate member, and further including a support adapter being removably mounted to said feeding device support member for supporting a feeding device, said elongate support member being removably and adjustably disposed in said bore of said first bracket and is securely fastened and engaged in said bore of said first bracket with said threaded member, said feeding device support member being generally a ring being disposed in a plane which is generally perpendicular to said elongate member, said support adapter including a cylinder having a bore extending therethrough and also having an annular flange being attached about a rim at a top end of said cylinder and being adapted to rest upon said ring with said bore of said cylinder being adapted to receive and support a feeding device, said elongate member having a generally square cross-section.

* * * * *